United States Patent
Schaetti et al.

(10) Patent No.: US 10,639,500 B2
(45) Date of Patent: May 5, 2020

(54) TARGET REGION PARTITIONING IN RADIATION THERAPY FOR MINIMISING IRRADIATION OF NON-TARGET TISSUE

(71) Applicant: Brainlab AG, Munich (DE)

(72) Inventors: Andreas Schaetti, Munich (DE); Stefan Schell, Munich (DE); Robert Grummt, Munich (DE)

(73) Assignee: Brainlab AG, Munich (DE)

( * ) Notice: Subject to any disclaimer, the term of this patent is extended or adjusted under 35 U.S.C. 154(b) by 427 days.

(21) Appl. No.: 15/548,059

(22) PCT Filed: Oct. 15, 2015

(86) PCT No.: PCT/EP2015/073854
§ 371 (c)(1),
(2) Date: Aug. 1, 2017

(87) PCT Pub. No.: WO2017/063699
PCT Pub. Date: Apr. 20, 2017

(65) Prior Publication Data
US 2018/0028837 A1  Feb. 1, 2018

(51) Int. Cl.
*A61N 5/10* (2006.01)
(52) U.S. Cl.
CPC .......... *A61N 5/103* (2013.01); *A61N 5/1047* (2013.01); *A61N 2005/1087* (2013.01)
(58) Field of Classification Search
CPC .................. A61N 5/103; A61N 5/1047; A61N 2005/1087
See application file for complete search history.

(56) References Cited

U.S. PATENT DOCUMENTS

| | | |
|---|---|---|
| 2005/0267358 A1 | 12/2005 | Tuma et al. |
| 2007/0081629 A1 | 4/2007 | Yin et al. |
| 2008/0310590 A1 | 12/2008 | Meyer et al. |

(Continued)

FOREIGN PATENT DOCUMENTS

| | | |
|---|---|---|
| EP | 0695560 A2 | 2/1996 |
| EP | 1563799 A1 | 8/2005 |

(Continued)

OTHER PUBLICATIONS

International Search Report and Written Opinion from corresponding International Application No. PCT/EP2015/073854, dated Jun. 13, 2016. 10 pages.

(Continued)

*Primary Examiner* — Qian Yang
(74) *Attorney, Agent, or Firm* — Tucker Ellis LLP (57) ABSTRACT

Disclosed is a method for determining an irradiation trajectory for the movement of a treatment device for irradiating an anatomical structure with ionising treatment radiation, the method comprising steps of
acquiring medical image data describing a medical image of the anatomical structure;
determining, based on the medical image data, image concavity data;
acquiring predetermined concavity data;
determining, based on the image concavity data and the predetermined concavity data, partition data;
determining, based on the medical image data, partition boundary data; and
determining, based on the partition boundary data, irradiation trajectory data.

18 Claims, 4 Drawing Sheets

(56) References Cited

U.S. PATENT DOCUMENTS

2013/0016092 A1*  1/2013  Collins ............... A61B 8/0891
                                                    345/419
2013/0150647 A1   6/2013  Chen et al.

FOREIGN PATENT DOCUMENTS

| EP | 1909904 A1 | 4/2008 |
| WO | 2007012185 A1 | 2/2007 |
| WO | 2015039903 A1 | 3/2015 |

OTHER PUBLICATIONS

Liu, et al., "Convex Shape Decomposition", 2010, IEEE, pp. 97-104. 8 pages.

Li, et al., "Decomposing Polygon Meshes for Interactive Applications", ACM Symp. on Interactive 3D Graphics, pp. 35-42.pp. 243, NC, Mar. 19-21, 2001. 9 pages.

Arganda-Carreras, et al., "ANALYZESKELETON—Analysis of 2D and 3D skeleton images", 2017, GitHub, Retrieved from "http://imagej.net/index.php?title=AnalyzeSkeleton&oldid=32884". 8 pages.

Arganda-Carreras, et al., "3D Reconstruction of Histological Sections: Application to Mammary Gland Tissue", 2010, Microscopy Research and Technique, pp. 1019-1029, 12 pages.

Arganda-Carreras, et al., "SKELETONIZE3D—2D and 3D skeletonization of binary images", 2017, GitHub, Retrieved from "http://imagej.net/index.php?title=Skeletonize3D&oldid=32558". 3 pages.

Lee, et al., "Building Skeleton Models via 3-D Medial Surface/Axis Thinning Algorithms", Graphical Models and Image Processing, vol. 56, No. 6, November, pp. 462-478. 1994, Academic Press, Inc. 17 pages.

GitHud, "Skeletonize3D", https://github.com/fiji/Skeletonize3D, 2017, retrieved from the internet on Jul. 25, 2017. 1 page.

* cited by examiner

TARGET REGION PARTITIONING IN RADIATION THERAPY FOR MINIMISING IRRADIATION OF NON-TARGET TISSUE

RELATED APPLICATION DATA

This application is a national phase application of International Application No. PCT/EP2015/073854 filed Oct. 15, 2015 and published in the English language.

The present invention is directed to a computer-implemented method for determining an irradiation trajectory for the movement of a treatment device for irradiating an anatomical structure with ionising treatment radiation, a corresponding computer program, a non-transitory program storage medium storing such a program and a computer for executing the program, as well as a system for controlling an irradiation therapy device comprising a database and such a computer.

TECHNICAL BACKGROUND

In radiation treatment planning, using either intensity-modulated radiation therapy (IMRT) or volumetric modulated arc therapy (VMAT) it is difficult to create satisfactory treatment plans for target volumes with concave parts. More specifically, healthy tissue in the vicinity of those concave parts of the target volume is unnecessarily irradiated. In addition, the geometric shapes of the irradiation fields may be more complicated for target volumes with concave parts. The plans can be manually improved by adding dummy risk volumes at those locations of the healthy tissue where irradiation is too high. Alternatively the plans can be manually improved by using a higher number of treatment beams that irradiate different parts of the target volume. This can be achieved either by limiting the leaf travel of the multi-leaf collimator (MLC) leaves for each beam or by manually setting the jaws of the MLC to restrict leaf motion of the beams.

An object of the invention therefore is to provide a method of determining a trajectory of a treatment device for radiation therapy which automatically seeks to avoid irradiation of tissue lying outside the target region while allowing for an optimal coverage of the target region with ionising treatment radiation.

Aspects of the present invention, examples and exemplary steps and their embodiments are disclosed in the following. Different advantageous features can be combined in accordance with the invention wherever technically expedient and feasible.

Exemplary Short Description of the Present Invention

In the following, a short description of the specific features of the present invention is given which shall not be understood to limit the invention only to the features or a combination of the features described in this section.

The disclosed method encompasses determining a measure of concavity for a target region which comprises the target of a radiation treatment in order to determine whether the target region needs dividing (partitioning) in order to avoid undesired administration of ionising radiation to tissue outside the target region (non-target tissue). The method includes deciding whether the target region needs to be partitioned (i.e. divided) into target region partitions. The positions of the target region partitions serve as a basis for determining a trajectory of a treatment device for radiation therapy of the target region, wherein at least one trajectory is determined for each of the target region partitions.

General Description of the Present Invention

In this section, a description of the general features of the present invention is given for example by referring to possible embodiments of the invention.

In general, the invention reaches the aforementioned object by providing, in a first aspect, a computer-implemented method for determining an irradiation trajectory for the movement of a treatment device for irradiating an anatomical structure with ionising treatment radiation. The method comprises executing, on at least one processor of at least one computer, the following exemplary steps which are executed by the at least one processor.

In a (for example first) exemplary step, medical image data is acquired which describes (for example represents or defines) a medical image of the anatomical structure, wherein the anatomical structure comprises both a target region (comprising for example tumour tissue) which is a target of the irradiation and non-target tissue, wherein irradiation of the non-target tissue shall be avoided. The anatomical structure can be located in any body part and can comprise at least one of soft tissue (such as skin, brain matter or an internal organ) and hard tissue (such as bone tissue or cartilage). The non-target comprises (specifically, consists of) normal tissue which is tissue within the patient that is not supposed to be irradiated but still receives a certain amount of dose nevertheless. This unwanted tissue irradiation exists because it is technically not possible to have dose only in the target region (the planning treatment volume PTV) and no dose anywhere else. By definition, normal tissue is used to refer to tissue outside the PTV. The non-target tissue is generally disjoint from the target region and may but need not necessarily comprise specific risk regions (organs-at-risk, i.e. organs which must not be irradiated during the medical procedure if a particular risk to the patient is to be avoided). The medical image data may be patient-specific which has been generated by applying a medical imaging modality (such as magnetic resonance tomography or computed x-ray tomography, conventional x-ray imaging or ultrasound imaging) to the specific patient's anatomical structure. Alternatively, the medical imaging data may not be patient-specific, for example if the medical image data comprises (specifically, consists of) atlas data describing (for example, representing or defining) an image-based model of the anatomical structure which has been generated for example from medical images generated for a population of patients. The medical image data in one example is three-dimensional image data but may alternatively be two-dimensional image data (for example, if it has been generated by conventional x-ray imaging).

In a further (for example second) exemplary step, image concavity data is determined which describes (for example represents or defines) a value of a measure of concavity of at least part of the target region described by the medical image. The image concavity data is determined based on (for example from) the medical image data. The measure of concavity indicates how much non-target tissue lies in concavities of the target region and may therefore be subject to undesired irradiation because it may be included in the region to which an irradiation dose may be assigned during dose planning. This may happen for example for small cavities in the exterior boundary of the target region because the optimisation algorithm for determining the irradiation dose distribution cannot exclude those cavities from being irradiated. It is an object of the disclosed method to minimise (specifically, eliminate) such an effect. The image concavity data is in one embodiment of this exemplary step determined by determining the value of a concavity measure defined as a ratio of the volume of a convex hull of the target region and the volume of the target region. The concavity is defined as the topological concavity of the target region which is a measure for expressing how much of the target region has a concave shape. For example, the convex hull is defined by all image units that lie on a straight line between any two image units (such as pixels or voxels) of the at least part of the target region. A concave shape is the opposite of a convex shape. In Euclidean space, a convex set (a convex shape) is a region such that, for every pair of points within the region, every point on the straight line segment that joins the pair of points is also within the region. For example, a solid cube is a convex set, but anything that is hollow or has a dent in it, for example, a crescent shape, is not convex. A convex curve forms the boundary of a convex set. The convex hull or convex envelope of a set X of points in the Euclidean plane or Euclidean space is the smallest convex set that contains X. Thus, the convex hull of the at least part of the target region is the smallest convex volume that contains all (discrete) points (such as image units represented by pixels or voxels) in the target region. Within the framework of the disclosed method, it is also possible to use other measures describing the concavity such as the average curvature of the surface of the target region.

In a further (for example third) exemplary step, predetermined concavity data is acquired which describes (for example, represents or defines) a predetermined value of the measure of concavity for the at least part of the target region. The predetermined value is a maximum value of the measure of concavity. The maximum value is considered a value which is tolerable without a need for partitioning the target region. This value is read by the disclosed method as an input value for example from a stored dataset.

In a further (for example fourth) exemplary step, partition data is determined which describes (for example indicates or defines) whether the at least part of the target region is to be partitioned into target region partitions. The partition data is determined based on the image concavity data and the predetermined concavity data. For example, the value of the measure of concavity described by the image concavity data is compared to the predetermined value of the measure of concavity described by the predetermined concavity data. If the comparison results in that the value of the measure of concavity described by the image concavity data is larger than the predetermined value of the measure of concavity described by the predetermined concavity data, the partition data is determined to describe that the at least part of the target region is to be partitioned into for example two partitions. If the comparison results in that the value of the measure of concavity described by the image concavity data is not larger than the predetermined value of the measure of concavity described by the predetermined concavity data, the partition data is determined to describe that the at least part of the target region is not to be partitioned. In the latter case, the method may continue determining the irradiation trajectory data as described below.

If the partition data describes (i.e. if the portioning data is determined to describe) that the target region is to be partitioned, the method continues to determining, in a further (for example fifth) exemplary step and based on the medical image data, partition boundary data which describes (for example represents or defines) the position of a partition boundary between the target region partitions (into which the target region is to be partitioned). For example, the partition boundary data is determined if the aforementioned comparison results in that the value of the measure of the concavity described by the image concavity data is greater than the value of the measure of the concavity described by the predetermined concavity data. The position of the partition boundary is defined for example in a reference system in which positions in the medical image are defined.

In one example of this exemplary step, the partition boundary data is determined by determining, for each image unit (such as each pixel or each voxel) in the medical image representing the target region, possibilities for positioning a boundary between target region partitions such that the sum of all individual concavities of the target region partitions is less than the concavity of the target region as a whole.

In the same or another example, the partition boundary data is determined by applying a skeletonizing algorithm to the representation of the target region in the medical image, and defining the boundary between the target region partitions such that a plane representing the boundary passes through an image unit on the skeleton. The skeleton is a representation of the target volume that captures the main geometric and topological features. For example, the skeleton of a sphere is a point, the skeleton of a cylinder is a line (with branches at the two ends), and the skeleton of a torus is a circle. The intersection of the plane representing the boundary with the target region near (i.e. within a predetermined neighbourhood around) this image unit on the skeleton is minimized. Alternatively, the plane representing the boundary is determined as passing through an image unit on the skeleton and being positioned in a direction perpendicular to the direction in which the part of the skeleton extends. A skeletonizing algorithm suitable for this application is disclosed in Lee, T. et al., Building Skeleton Models via 3-D Medial Surface/Axis Thinning Algorithms, Graphical Models and Image Processing, vol. 56, no. 6, November 1994, pp. 462-478. An implementation of the disclosed method uses the skeletonizing algorithm provided for the ImageJ image processing software. This algorithm is embodied in AnalyzeSkeleton and Skeletonize3D plugins for ImageJ (described at http://fiji.sc/AnalyzeSkeleton and http://fiji.sc/Skeletonize3D, respectively, and available as code at https://github.com/fiji/AnalyzeSkeleton and https://github.com/fiji/Skeletonize3D, respectively).

In an example, determining the partition boundary data comprises:
  determining, based on the medical image data and the partition boundary data, concavity sum data describing (for example, representing or defining) the sum of concavities of all target region partitions;
  determining, based on the concavity sum data and the image concavity data, whether the sum of concavities (i.e. the sum of the values of the measure of concavity, which can be determined in analogy to the above description of the second exemplary step) of all target region partitions is less than the concavity of the at least part of the target region; and
  if the result is that the sum of concavities of all target region partitions is less than the concavity of the at least part of the target region, accepting the assumed position of the boundary for further processing and stopping further partitioning of the at least part of the target region.

Thereby, it is assured that iterative execution of the disclosed method is stopped when an optimum of the concavity is achieved over the whole set of target region partitions.

The disclosed method may be applied iteratively, for example in order to partition the target region into more and more target region partitions with each iteration of executing the method. In an example of the disclosed method, the at least part of the target region is itself a target region partition determined by executing the aforementioned exemplary steps (for example, the first to fourth exemplary steps).

For example, the method may comprise the following steps, which are directed specifically to determining when repeated execution of the first to fourth exemplary steps shall be stopped, for example if a maximum (or minimum) number of partitions into which the target region shall be divided has been reached:

acquiring maximum target region partition data describing (for example representing or defining) a predetermined maximum number of target region partitions (which may be for example four, but also other integer numbers are within the framework of the disclosed method) into which the target region may be partitioned (alternatively, minimum target region partition data defining a predetermined minimum number of target region partitions into which the target region shall be partitioned may be acquired);

determining based on the partition boundary data, target region partition number data describing (for example, representing or indicating) the number of target region partitions into which the target region has already been partitioned (for example, the boundaries defined by the partition boundary data may be analysed by for example an image segmentation algorithm or edge detection algorithm in order to determine the number of such target region partitions);

determining, based on the maximum target region partition data (or based on the minimum target region partition data) and the target region partition number data (for example, by comparing the predetermined maximum number of target region partitions to the number of target region partitions into which the target region has already been partitioned), target region number comparison data indicating whether the number of target region partitions into which the target region has already been partitioned is greater than or equal to the maximum number of target region partitions into which the target region may be partitioned (or smaller than the minimum number of target region partitions into which the target region shall be partitioned);

wherein the partition data is determined to describe that the at least part of the target region is not to be partitioned into target region partitions if the target region number comparison data indicates that the number of target region partitions into which the target region has already been partitioned is greater than or equal to the (predetermined) maximum number of target region partitions into which the target region may be partitioned, or wherein the partition data is determined to describe that the at least part of the target region is to be partitioned into target region partitions if the target region number comparison data indicates that the number of target region partitions into which the target region has already been partitioned is smaller than the (predetermined) minimum number of target region partitions into which the target region shall be partitioned.

In a further (for example sixth) exemplary step, irradiation trajectory data is determined based on the partition boundary data. The irradiation trajectory data describes (for example represents or defines) at least one trajectory of the treatment device (such as an irradiation therapy device) usable for irradiating a target region partition with the ionising treatment radiation. The trajectory defines a path along which the treatment device (such as the emission unit of a particle accelerator) shall move when irradiating the target region for radiation treatment. The irradiation trajectory data is determined in particular on the basis of the positional information contained in the boundary position data such that appropriate movement of the treatment device is generated when the irradiation trajectory data is used as an input for controlling the treatment device. Additionally, the medical image data may serve as a basis for initially positioning the patient relative to the treatment device if the position of the treatment device has been transformed into the reference system used for defining positions in the medical image data or vice versa. This may be done by taking x-ray images of the patient while pre-positioning him on a patient bed associated with the treatment device.

The at least one trajectory is determined individually (i.e. specifically) for each target region partition. For example, patient couch angle data, treatment device movement range data and collimator angle data can be acquired as an additional basis for determining all possible irradiation trajectories of the target region. For example, predetermined trajectory data describing (for example, representing or defining) a set of predetermined trajectories for irradiating the target region may be acquired. The predetermined trajectory data may serve as optional additional basis for determining the irradiation trajectory data. For example, the irradiation trajectory may be determined by optimising a predetermined trajectory so that the treatment beam covers the at least part of the target region as desired. Each of these predetermined irradiation trajectories is then assigned to each target region partition, where the patient couch angle data, treatment device movement range data and collimator angle data of the original irradiation trajectories is used. The MLC leaf position data is determined such that all leaves are positioned in a certain distance from the boundary of the target region partition. For example, the distance might be zero. Alternatively, the distance might be a non-zero constant for all leaves of the beam collimator.

Alternatively, patient couch angle data, treatment device movement range data and collimator angle data is determined from the target region partitions. For example, all of these parameters might be optimized in order to avoid collision between the treatment device and the patient and to reduce or avoid irradiation of non-target tissue, specifically organs-at-risk.

Irradiation of a target region partition may also be covered by more than one trajectory. However, each determined trajectory is determined specifically according to the position of only one target region partition. This provides the advantage that the whole target region can be irradiated more accurately than possible with prior art approaches. In particular, the treatment beam is less likely to traverse non-target tissue if the at least one trajectory is determined in accordance with the disclosed method.

The disclosed method may in another example comprise determining, based on the irradiation trajectory data, treatment plan data describing a treatment plan for conducting a medical procedure including irradiation of the anatomical structure with ionising radiation, for example radiotherapy or radiosurgery. A treatment plan comprises further information on how treatment of a patient with ionising treatment radiation is to be effected. For example, the treatment plan defines not only the positions and dose values of a dose distribution to be administered but also the number of fractions to be administered to the patient and the time intervals between individual fractions.

In a second aspect, the invention is directed to a computer program which, when running on at least one processor (for example, a processor) of at least one computer (for example, a computer) or when loaded into at least one memory (for example, a memory) of at least one computer (for example, a computer), causes the at least one computer to perform the above-described method according to the first aspect.

In a third aspect, the invention is directed to a non-transitory computer-readable program storage medium on which the program according to the second aspect is stored.

In a fourth aspect, the invention is directed to at least one computer (for example, a computer), comprising at least one processor (for example, a processor) and at least one memory (for example, a memory), wherein the program according to the second aspect is running on the processor or is loaded into the memory, or wherein the at least one computer comprises the program storage medium according to the third aspect.

In a fifth aspect, the invention is directed to a system for controlling an irradiation therapy device for use in a medical procedure involving irradiation of an anatomical structure with ionising radiation. The system comprises:
a) the at least one computer according to the fourth aspect;
b) at least one electronic data storage device storing the medical image data and the predetermined concavity data,
wherein the at least one computer is operably coupled to the at least one electronic data storage device for acquiring, from the at least one electronic data storage device, the medical image data and the predetermined concavity data; and
c) the irradiation therapy device which is configured to emit a beam of ionising treatment radiation,
wherein the computer is operatively coupled to the irradiation therapy device so as to effect emission of the treatment radiation by the irradiation therapy device based on the irradiation trajectory data.

The disclosed method removes the root cause for irradiation of non-target tissue in the proximity of the target region, namely the presence of concave parts of the target volume. Locations in the target volume are determined so that dividing the target volume at these locations creates parts that are less concave, i.e. more convex, than the original target volume. No user interaction is necessary. Target beams that the user has assigned to the original target are automatically copied and assigned to the parts.

The disclosed method uses a novel approach to convex decomposition of objects, namely searching locations to divide the target volume only on the skeleton of the target volume and identify the best locations by minimizing the concavity of the parts resulting from the divisions (partitions).

If the target volume has a concavity below a certain threshold then no division may be necessary. In this case, the optimization algorithm will not significantly improve the treatment plan by using a divided target volume.

In order to reduce the number of possible divisions the division plane at each location may be predetermined. A possible criterion to predetermine a division plane is to find the plane going through the location that minimizes the intersection of the plane with the target region near the location.

Instead of using a skeleton, all locations inside the target volume may be allowed but the possible orientations of division planes that pass through the locations may be restricted to a few orientations, e.g. anterior-posterior and left-right planes.

It may be advantageous to align the division plane to the treatment beam geometry to improve the result of leaf sequencing. It may also be advantageous to use anatomical information of the target volume or risk volumes in the vicinity of the target volume to improve the result of the division.

For target volumes that do not contain a hole that penetrates the whole volume of the target region, e.g. similar to a sphere, the method is implemented iteratively where only one division is performed in each step resulting in two parts. Each resulting part of a division is again divided if necessary.

For target volumes that contain a hole that penetrates the whole volume, e.g. similar to a torus, in the first iteration at least two division locations are necessary to generate at least two parts. These locations are searched simultaneously. Further divisions are also searched simultaneously, i.e., dividing either of the part twice and not dividing the other part is compared with dividing both parts once.

There are many possible divisions of a target volume into parts. An efficient way to find the best locations to divide the target volume is to analyze the skeleton of the target volume. The number of locations on the skeleton is much smaller than the number of all possible locations inside the target volume. Thus the algorithm works much faster and is more likely to find divisions that seem reasonable or natural to a human, i.e., the result looks more similar to the division that a human may have performed intuitively. In addition, the algorithm is fully automatic.

The treatment plan generated by the optimization algorithm using the target volume divided into parts with higher convexity is in general much better in terms of target volume coverage, dose gradient outside the target volume and dose to healthy tissue than the corresponding treatment plan when using the original target volume. For convex target volumes the algorithm may determine that the improvement of the optimization result may be not significant and that the target volume shall not be divided. The benefit of not dividing the target volume may be that the number of treatment beams does not increase and that the total number of monitor units applied to the patient may be lower, leading to less leakage and stray irradiation of the patient. A monitor unit is the smallest unit of photon fluence that a radiation therapy device can produce. It is linked to a certain dose at a certain depth for a certain aperture size of the radiation therapy device in a certain quality assurance device. Monitor units are not directly linked to the dose in patients because the aperture can be highly modulated. Large monitor units are usually associated with small apertures and therefore more leakage and stray irradiation of the patient.

It is within the scope of the present invention to combine one or more features of one or more embodiments or aspects of the invention in order to form a new embodiment wherever this is technically expedient and/or feasible. Specifically, a feature of one embodiment which has the same or a similar function to another feature of another embodiment can be exchanged with said other feature, and a feature of one embodiment which adds an additional function to another embodiment can for example be added to said other embodiment.

Definitions

In this section, definitions for specific terminology used in this disclosure are offered which also form part of the present disclosure.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

The method in accordance with the invention is for example a computer implemented method. For example, all the steps or merely some of the steps (i.e. less than the total number of steps) of the method in accordance with the invention can be executed by a computer (for example, at least one computer). An embodiment of the computer implemented method is a use of the computer for performing a data processing method. The computer for example comprises at least one processor and for example at least one memory in order to (technically) process the data, for example electronically and/or optically. The processor being for example made of a substance or composition which is a semiconductor, for example at least partly n- and/or p-doped semiconductor, for example at least one of II-, III-, IV-, V-, VI-semiconductor material, for example (doped) silicon and/or gallium arsenide. The calculating steps described are for example performed by a computer. Determining steps or calculating steps are for example steps of determining data within the framework of the technical method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is an augmented reality device (also referred to as augmented reality glasses) which can be used as "goggles" for navigating. A specific example of such augmented reality glasses is Google Glass (a trademark of Google, Inc.). An augmented reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. The monitor may also be the monitor of a portable, for example handheld, device such as a smart phone or personal digital assistant or digital media player.

The expression "acquiring data" for example encompasses (within the framework of a computer implemented method) the scenario in which the data are determined by the computer implemented method or program. Determining data for example encompasses measuring physical quantities and transforming the measured values into data, for example digital data, and/or computing the data by means of a computer and for example within the framework of the method in accordance with the invention. The meaning of "acquiring data" also for example encompasses the scenario in which the data are received or retrieved by the computer implemented method or program, for example from another program, a previous method step or a data storage medium, for example for further processing by the computer implemented method or program. The expression "acquiring data" can therefore also for example mean waiting to receive data and/or receiving the data. The received data can for example be inputted via an interface. The expression "acquiring data" can also mean that the computer implemented method or program performs steps in order to (actively) receive or retrieve the data from a data source, for instance a data storage medium (such as for example a ROM, RAM, database, hard drive, etc.), or via the interface (for instance, from another computer or a network). The data acquired by the disclosed method or device, respectively, may be acquired from a database located in a data storage device which is operably to a computer for data transfer between the database and the computer, for example from the database to the computer. The computer acquires the data for use as an input for steps of determining data. The determined data can be output again to the same or another database to be stored for later use. The database or database used for implementing the disclosed method can be located on network data storage device or a network server (for example, a cloud data storage device or a cloud server) or a local data storage device (such as a mass storage device operably connected to at least one computer executing the disclosed method). The data can be made "ready for use" by performing an additional step before the acquiring step. In accordance with this additional step, the data are generated in order to be acquired. The data are for example detected or captured (for example by an analytical device). Alternatively or additionally, the data are inputted in accordance with the additional step, for instance via interfaces. The data generated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, for example determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

Atlas data describes (for example defines, more particularly represents and/or is) a general three-dimensional shape of the anatomical body part. The atlas data therefore represents an atlas of the anatomical body part. An atlas typically consists of a plurality of generic models of objects, wherein the generic models of the objects together form a complex structure. For example, the atlas constitutes a statistical model of a patient's body (for example, a part of the body) which has been generated from anatomic information gathered from a plurality of human bodies, for example from medical image data containing images of such human bodies. In principle, the atlas data therefore represents the result of a statistical analysis of such medical image data for a plurality of human bodies. This result can be output as an image—the atlas data therefore contains or is comparable to medical image data. Such a comparison can be carried out for example by applying an image fusion algorithm which conducts an image fusion between the atlas data and the medical image data. The result of the comparison can be a measure of similarity between the atlas data and the medical image data.

The human bodies, the anatomy of which serves as an input for generating the atlas data, advantageously share a common feature such as at least one of gender, age, ethnicity, body measurements (e.g. size and/or mass) and pathologic state. The anatomic information describes for example the anatomy of the human bodies and is extracted for example from medical image information about the human bodies. The atlas of a femur, for example, can comprise the head, the neck, the body, the greater trochanter, the lesser trochanter and the lower extremity as objects which together make up the complete structure. The atlas of a brain, for example, can comprise the telencephalon, the cerebellum, the diencephalon, the pons, the mesencephalon and the medulla as the objects which together make up the complex structure. One application of such an atlas is in the segmentation of medical images, in which the atlas is matched to medical image data, and the image data are compared with the matched atlas in order to assign a point (a pixel or voxel) of the image data to an object of the matched atlas, thereby segmenting the image data into objects.

The present invention relates to the field of controlling a treatment beam. The treatment beam treats body parts which are to be treated and which are referred to in the following as "treatment body parts". These body parts are for example parts of a patient's body, i.e. anatomical body parts.

In the field of medicine, imaging methods (also called imaging modalities and/or medical imaging modalities) are used to generate image data (for example, two-dimensional or three-dimensional image data) of anatomical structures (such as soft tissues, bones, organs, etc.) of the human body. The term "medical imaging methods" is understood to mean (advantageously apparatus-based) imaging methods (so-called medical imaging modalities and/or radiological imaging methods) such as for instance computed tomography (CT) and cone beam computed tomography (CBCT, such as volumetric CBCT), x-ray tomography, magnetic resonance tomography (MRT or MRI), conventional x-ray, sonography and/or ultrasound examinations, and positron emission tomography. The image data thus generated is also termed "medical imaging data". Analytical devices for example are used to generate the image data in apparatus-based imaging methods. The imaging methods are for example used for medical diagnostics, to analyse the anatomical body in order to generate images which are described by the image data.

The imaging methods are also for example used to detect pathological changes in the human body. However, some of the changes in the anatomical structure, such as the pathological changes in the structures (tissue), may not be detectable and for example may not be visible in the images generated by the imaging methods. A tumour represents an example of a change in an anatomical structure. If the tumour grows, it may then be said to represent an expanded anatomical structure. This expanded anatomical structure may not be detectable; for example, only a part of the expanded anatomical structure may be detectable. Primary/high-grade brain tumours are for example usually visible on MRI scans when contrast agents are used to infiltrate the tumour. MRI scans represent an example of an imaging method. In the case of MRI scans of such brain tumours, the signal enhancement in the MRI images (due to the contrast agents infiltrating the tumour) is considered to represent the solid tumour mass. Thus, the tumour is detectable and for example discernible in the image generated by the imaging method. In addition to these tumours, referred to as "enhancing" tumours, it is thought that approximately 10% of brain tumours are not discernible on a scan and are for example not visible to a user looking at the images generated by the imaging method.

The present invention relates to the field of controlling a treatment beam. The treatment beam treats body parts which are to be treated and which are referred to in the following as "treatment body parts". These body parts are for example parts of a patient's body, i.e. anatomical body parts.

The present invention relates to the field of medicine and for example to controlling beams, such as radiation beams, to treat parts of a patient's body, which are therefore also referred to as treatment beams, and the radiation is also called treatment radiation. A treatment beam treats body parts which are to be treated and which are referred to in the following as "treatment body parts". These body parts are for example parts of a patient's body, i.e. anatomical body parts or the above-mentioned anatomical structure. Ionising radiation is for example used for the purpose of treatment. For example, the treatment beam comprises or consists of ionising radiation. The ionising radiation comprises or consists of particles (for example, sub-atomic particles or ions) or electromagnetic waves which are energetic enough to detach electrons from atoms or molecules and so ionise them. Examples of such ionising radiation include x-rays, high-energy particles (high-energy particle beams) and/or ionising radiation emitted from a radioactive element. The treatment radiation, for example the treatment beam, is for example used in radiation therapy or radiotherapy, such as in the field of oncology. For treating cancer in particular, parts of the body comprising a pathological structure or tissue such as a tumour are treated using ionising radiation. The tumour is then an example of a treatment body part.

The treatment beam is preferably controlled such that it passes through the treatment body part. However, the treatment beam can have a negative effect on body parts outside the treatment body part. These body parts are referred to here as "outside body parts" or "non-target tissue". Generally, a treatment beam has to pass through outside body parts in order to reach and so pass through the treatment body part, specifically the target region.

DESCRIPTION OF THE FIGURES

In the following, the invention is described with reference to the appended figures which represent a specific embodiment of the invention. The scope of the invention is however not limited to the specific features disclosed in the context of the figures, wherein.

Figure 1:
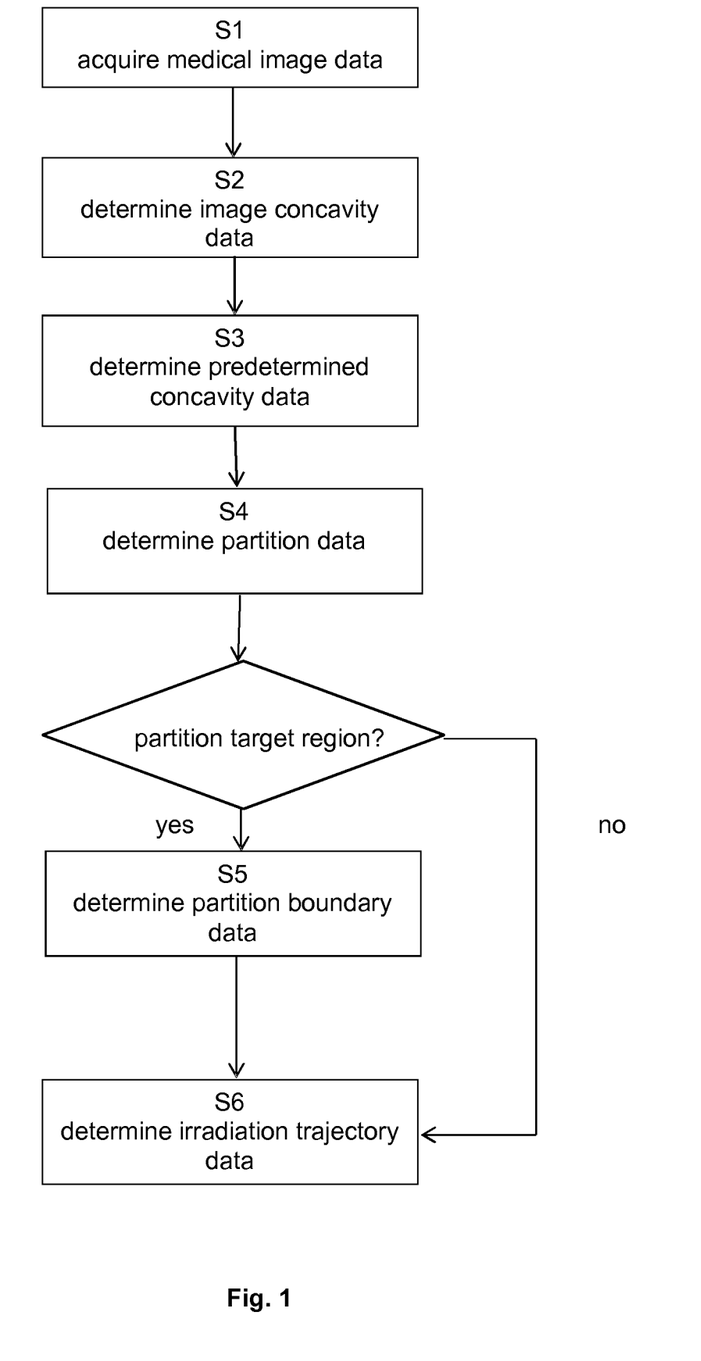
FIG. 1 is a flow diagram showing the steps of the disclosed method.

FIG. 1 shows the flow of the steps of the disclosed method. In step S1, the medical image data is acquired for example from a repository containing a database of patient-specific images or image-based atlas data. In step S2, the method continues to determining the image concavity data. The predetermined concavity data is read by the method in step S3, but may also be read at an earlier stage of executing the disclosed method. Step S4 encompasses determining whether the target region requires partitioning by comparing the values of the measure of concavity described by the image concavity data and the predetermined concavity data. The result of this comparison is written for example as a logical value to the partition data. This is followed by analysing the partition data as to whether the target region shall be partitioned. If this is the case ("yes"), the method continues to step S5 which is directed to determining the partition boundary data. The partition boundary data serves as an input for determining the irradiation trajectory data in steps S6. If it is determined that the target region shall not be partitioned ("no"), the method continues directly to step S6.

Figure 2:
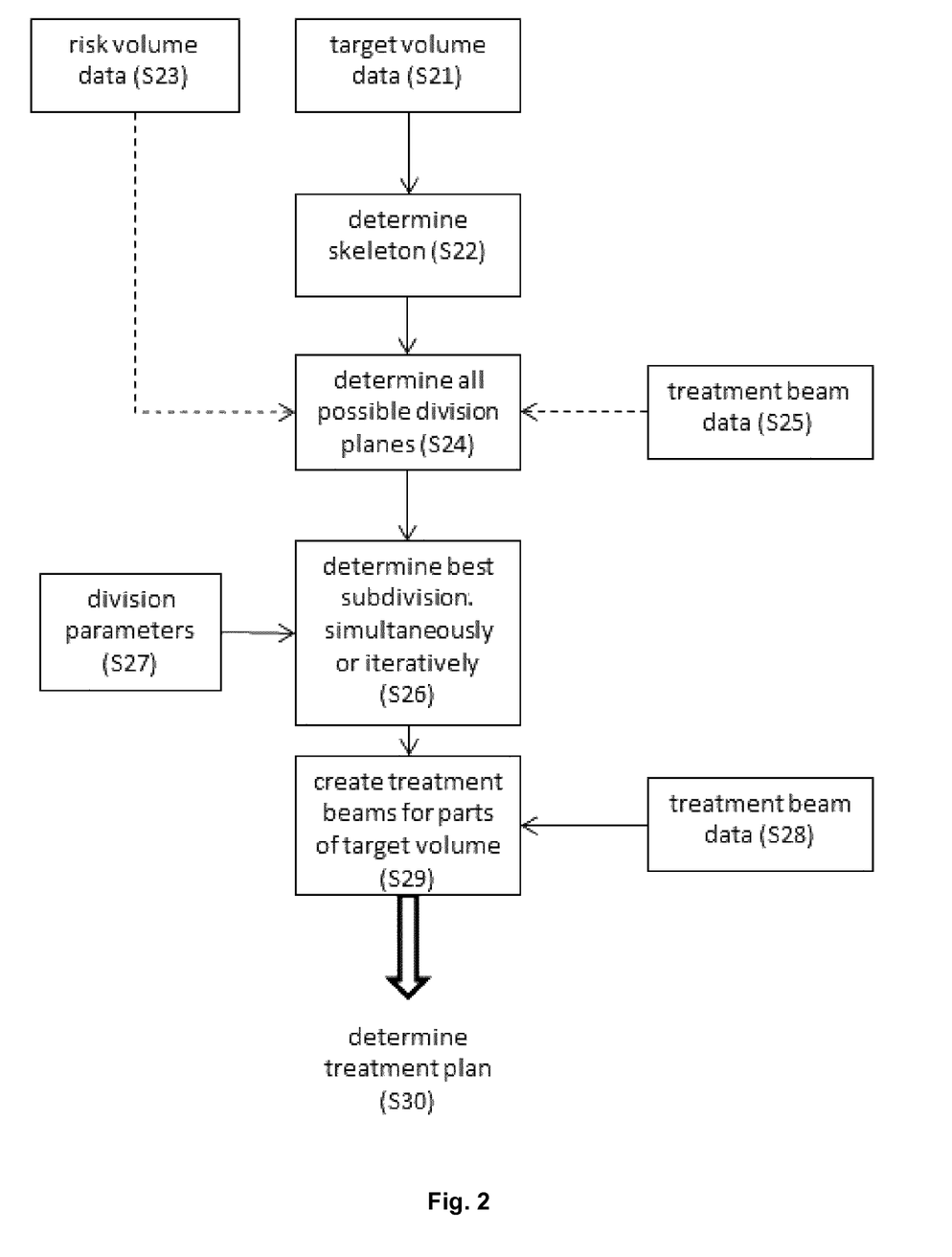
FIG. 2 is a flow diagram of an embodiment of the method of FIG. 1.

FIG. 2 illustrates a second embodiment of the disclosed method. The method starts with reading the medical image data and extracting target volume data which describes (for example, represents or defines) the position of the target region in the medical image. Step S22 comprises determining a skeleton of the target region as an embodiment of determining the partition boundary data. In the skeleton, all possible division planes representing the boundaries between target region partitions are determined as step S24, optionally taking into account the position of organs-at-risk (risk regions which shall be irradiated only as little as possible and are not part of the target region) which is described by risk volume data which is inputted in optional step S23. Step S24 takes into account for example further boundary conditions for determining the applicable partitioning, for example an anatomically meaningful orientation of a division plane. In optional step S25, the geometry and position of a treatment beam of ionising radiation is read as treatment beam data by the method in step S25 and taken into account in step S24. The method then continues to step S26 which is directed to determining the best subdivision (partitioning) of the target region. This may be done for a plurality of portioning options simultaneously or iteratively. A further input to step S26 is data describing (for example representing or defining) division parameters which is read in step S27. The division parameters may include the number of partitions into which the target region may be partitioned (embodied for example by the maximum target region partition data). The definitions of treatment beams for the parts of the target volume (i.e. the target region partitions) are then created by determining the irradiation trajectory data in step S29. This takes into account the treatment beam data which have either been optionally acquired in step S25 or have been acquired in step S28. The definitions of the treatment beams then serve as a basis for determining a treatment plan in step S30.

Figure 3:
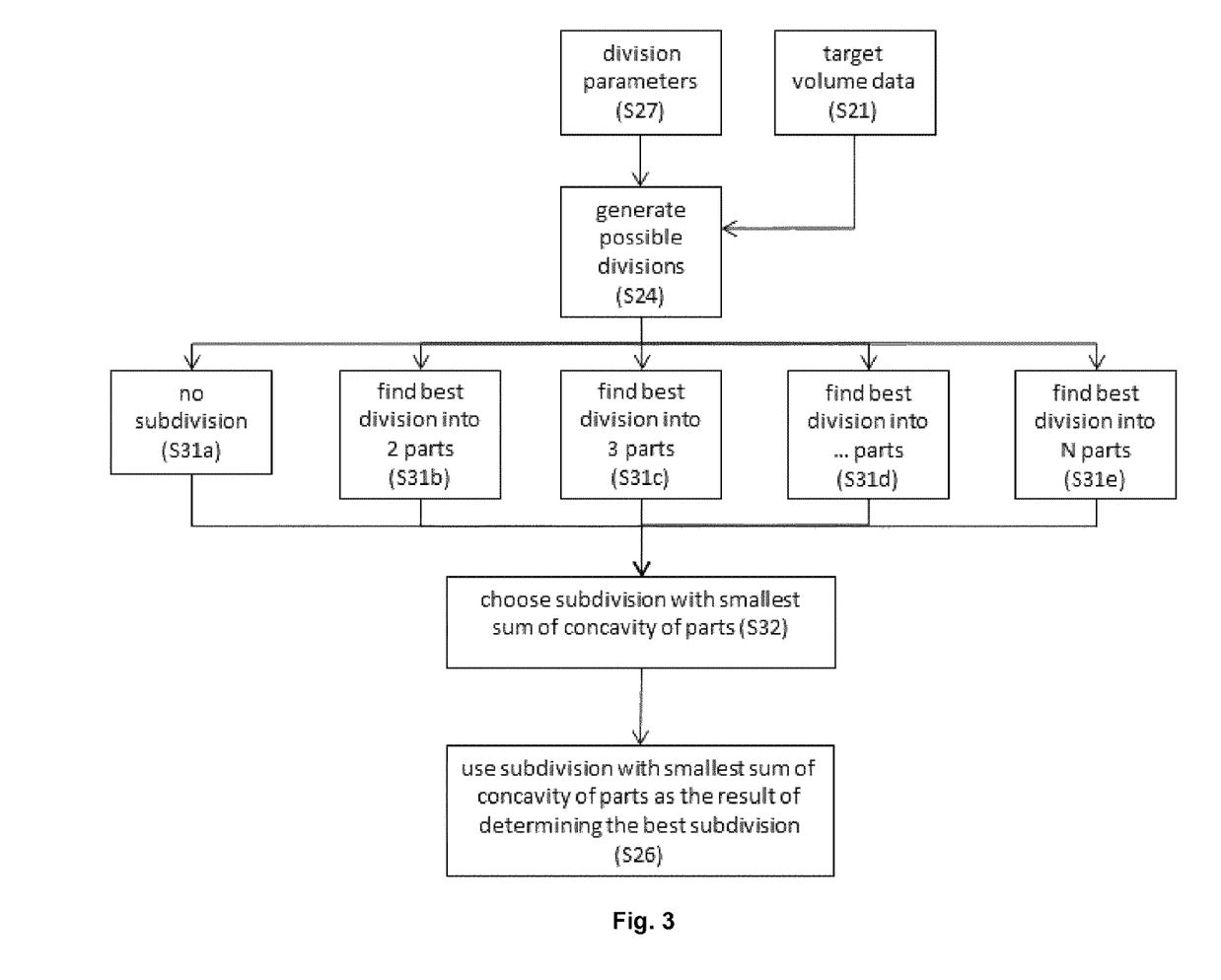
FIG. 3 shows an embodiment of choosing the best partitioning of the target region.

In FIG. 3, steps having the same reference signs as already used in FIG. 2 correspond to the respective steps of FIG. 2. FIG. 3 comprises steps S31a to S31e and S32 which constitute an example of simultaneously determining the best subdivision in step S26 of FIG. 2. The method may be implemented in a way that always determines all division planes simultaneously. The algorithm may search for the best division for several numbers of resulting parts. The at least part of the target region is first not partitioned (step S31a), then partitioned into two parts (step S31b), then partitioned into three parts (step S31c), and this sequence of partitioning is continued (step S31d) until the at least part of the target region is partitioned into N parts (step S31e), where N>1 and N is an integer. Out of the whole of the at least part of the target region received from step S31a and the partitions received from steps S31b through S31e, the result is chosen which has the smallest sum of concavity of its parts (i.e. of its target region partitions or sub-partitions of target region partitions) in step S32 as the best subdivision (i.e. partitioning) of the at least part of the target region. This best subdivision is used as the result of step S26.

Figure 4:
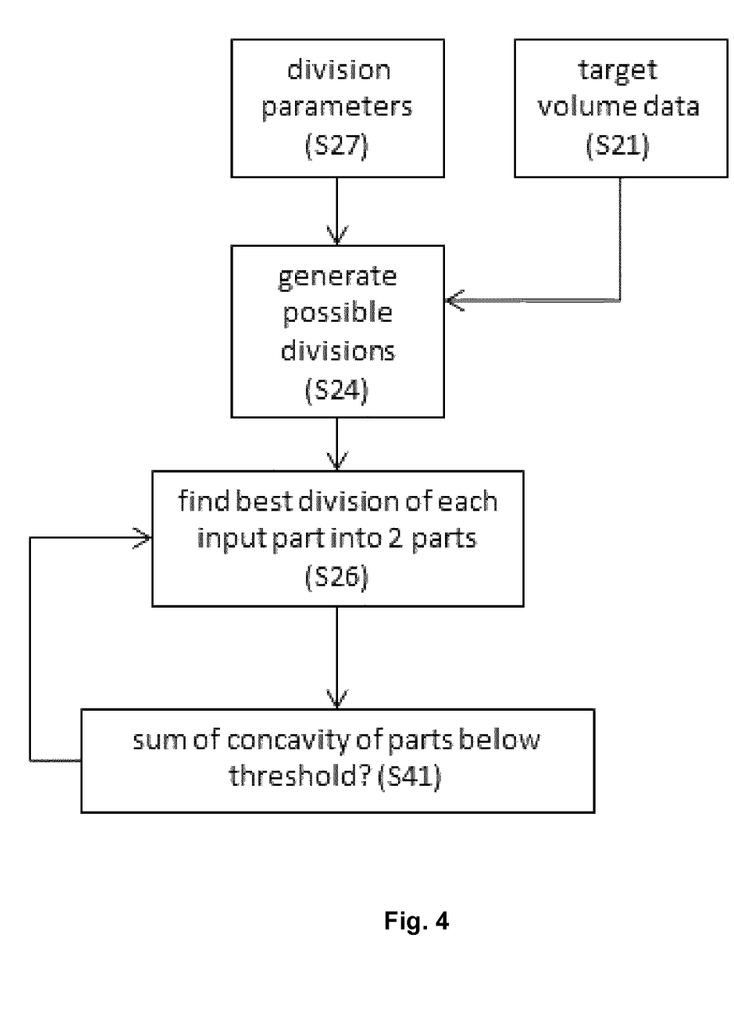
FIG. 4 is another embodiment of determining whether a certain partitioning fulfils a predetermined acceptance criterion.

The steps having same reference signs in both FIGS. 2 and 4 also have the same meaning as described in the context of FIG. 2. FIG. 4 shows how a predetermined acceptance criterion for determining whether a partitioning of the at least part of the target region shall be accepted as a basis for determining the irradiation trajectory data. This leads to iterative partitioning of the at least part of the target region. In this example, steps S26 is directed to dividing the at least part of the target region ("input part") into two partitions ("parts"). If step S41 determines that the sum of the concavities of the partitions is below a predetermined threshold (for example the predetermined value of the measure of concavity described by the predetermined concavity data), it is decided that no further partitioning of the partitions is necessary. Otherwise, it is decided that further partitioning of the partitions shall be determined and then re-analysed as to its acceptance in step S41. Thereby, the method scans through first the target region as a whole and then all subsequently determined target region partitions and the next generation(s) of target region partitions whether they can still be divided into further target region partitions without violating the predetermined acceptance criterion used as a threshold in step S41.

The invention claimed is:

1. A method for determining an irradiation trajectory for the movement of a treatment device for irradiating an anatomical structure with ionising treatment radiation, the method comprising executing, on at least one processor of at least one computer, steps of:
   a) acquiring, at the at least one processor, medical image data describing a medical image of the anatomical structure, wherein the anatomical structure comprises both a target region which defines a target of the irradiation and non-target tissue, wherein irradiation of the non-target tissue is to be avoided;
   b) determining, by the at least one processor and based on the medical image data, image concavity data describing a value of a measure of concavity of at least part of the target region described by the medical image;
   c) acquiring, at the at least one processor, predetermined concavity data describing a predetermined value of the measure of concavity for the at least part of the target region;
   d) determining, by the at least one processor and based on the image concavity data and the predetermined concavity data, partition data describing whether the at least part of the target region is to be partitioned into target region partitions, wherein the partition data is determined by comparing, by the at least one processor, the value of the measure of the concavity described by the image concavity data to the value of the measure of the concavity described by the predetermined concavity data;
   e) determining that the partitioning data describes that the target region is to be partitioned, and determining, by the at least one processor, in response to the determination that the target region is to be partitioned, and based on the medical image data, partition boundary data describing the position of a partition boundary between the target region partitions, wherein the position of the partition boundary is defined in a reference system in which positions in the medical image are defined; and
   f) determining, by the at least one processor and based on the partition boundary data, irradiation trajectory data describing at least one trajectory of the treatment device usable for irradiating a target region partition with the ionising treatment radiation, wherein at least one trajectory is determined individually for each target region partition.

2. The method according to claim 1, wherein the image concavity data is determined by determining, by the at least one processor, the value of a concavity measure defined as a ratio of the volume of a convex hull of the target region and the volume of the target region.

3. The method according to claim 2, wherein the concavity is the topological concavity such that the convex hull is defined by all image units that lie on a straight line between any two image units of the at least part of the target region.

4. The method according to claim 1, wherein the at least part of the target region is itself a target region partition determined by executing steps a) to e).

5. The method according to claim 1, wherein comparing the value of the measure of the concavity described by the image concavity data to the value of the measure of the concavity described by the predetermined concavity data comprises determining, by the at least one processor, whether the value of the measure of the concavity described by the image concavity data is greater than the predetermined value of the measure of the concavity described by the predetermined concavity data.

6. The method according to claim 5, wherein the partition boundary data is determined in response to a determination that the value of the measure of the concavity described by the image concavity data is greater than the value of the measure of the concavity described by the predetermined concavity data.

7. The method according to claim 1, comprising:
   acquiring, at the at least one processor, maximum target region partition data defining a predetermined maximum number of target region partitions into which the target region may be partitioned;
   determining, by the at least one processor and based on the partition boundary data, target region partition number data describing the number of target region partitions into which the target region has already been partitioned;
   determining, by the at least one processor and based on the maximum target region partition data and the target region partition number data, target region number comparison data indicating whether the number of target region partitions into which the target region has already been partitioned is greater than or equal to the maximum number of target region partitions into which the target region may be partitioned;

wherein the partition data is determined, by the at least one processor, to describe that the at least part of the target region is not to be partitioned into target region partitions, in response to a determination that the target region number comparison data indicates that the number of target region partitions into which the target region has already been partitioned is greater than or equal to the maximum number of target region partitions into which the target region may be partitioned.

8. The method according to claim 1, wherein determining the partition boundary data comprises:

determining, by the at least one processor and based on the medical image data and the partition boundary data, concavity sum data describing the sum of concavities of all target region partitions;

determining, by the at least one processor and based on the concavity sum data and the image concavity data, whether the sum of concavities of all target region partitions is less than the concavity of the at least part of the target region; and accepting the assumed position of the boundary for further processing and stopping further partitioning of the at least part of the target region in response to a determination that the sum of concavities of all target region partitions is less than the concavity of the at least part of the target region.

9. The method according claim 1, wherein the partition boundary data is determined by applying, by the at least one processor, a skeletonizing algorithm to the representation of the target region in the medical image, and defining the boundary between the target region partitions such that an intersection area between a plane, representing the boundary and passing through an image unit on the skeleton, and the target region near this image unit on the skeleton is minimized or such that the plane representing the boundary is determined as passing through an image unit on the skeleton and being positioned in a direction perpendicular to the direction in which the part of the skeleton extends.

10. The method according to claim 1, wherein the partition boundary data is determined by determining, by the at least one processor and for each image unit in the medical image representing the target region, possibilities for positioning a boundary between target region partitions such that the sum of all individual concavities of the target region partitions is less than the concavity of the target region as a whole.

11. The method according to claim 1, comprising:

determining, by the at least one processor and based on the irradiation trajectory data, treatment plan data describing a treatment plan for conducting a medical procedure including irradiation of the anatomical structure with ionising radiation.

12. The method according to claim 11, wherein the medical procedure is radiotherapy or radiosurgery.

13. A non-transitory computer-readable storage medium having stored thereon computer-executable instructions that, when executed, configure at least one processor to:

a) acquire medical image data describing a medical image of the anatomical structure, wherein the anatomical structure comprises both a target region which defines a target of the irradiation and non-target tissue, wherein irradiation of the non-target tissue is to be avoided;

b) determine, based on the medical image data, image concavity data describing a value of a measure of concavity of at least part of the target region described by the medical image;

c) acquire predetermined concavity data describing a predetermined value of the measure of concavity for the at least part of the target region;

d) determine, based on the image concavity data and the predetermined concavity data, partition data describing whether the at least part of the target region is to be partitioned into target region partitions, wherein the partition data is determined by comparing the value of the measure of the concavity described by the image concavity data to the value of the measure of the concavity described by the predetermined concavity data;

e) determine that the partitioning data describes that the target region is to be partitioned, and further determine, in response to the determination that the target region is to be partitioned, and based on the medical image data, partition boundary data describing the position of a partition boundary between the target region partitions, wherein the position of the partition boundary is defined in a reference system in which positions in the medical image are defined; and f) determine, based on the partition boundary data, irradiation trajectory data describing at least one trajectory of the treatment device usable for irradiating a target region partition with the ionising treatment radiation, wherein at least one trajectory is determined individually for each target region partition.

14. A system for controlling an irradiation therapy device for use in a medical procedure involving irradiation of an anatomical structure with ionising radiation, the system comprising:

at least one processor configured to:

a) acquire medical image data describing a medical image of the anatomical structure, wherein the anatomical structure comprises both a target region which defines a target of the irradiation and non-target tissue, wherein irradiation of the non-target tissue is to be avoided;

b) determine, based on the medical image data, image concavity data describing a value of a measure of concavity of at least part of the target region described by the medical image;

c) acquire predetermined concavity data describing a predetermined value of the measure of concavity for the at least part of the target region;

d) determine, based on the image concavity data and the predetermined concavity data, partition data describing whether the at least part of the target region is to be partitioned into target region partitions, wherein the partition data is determined by comparing the value of the measure of the concavity described by the image concavity data to the value of the measure of the concavity described by the predetermined concavity data;

e) determine that the partitioning data describes that the target region is to be partitioned, and further determine, in response to the determination that the target region is to be partitioned, and based on the medical image data, partition boundary data describing the position of a partition boundary between the target region partitions, wherein the position of the partition boundary is defined in a reference system in which positions in the medical image are defined; and f) determine, based on the partition boundary data, irradiation trajectory data describing at least one trajectory of the treatment device usable for irradiating a target region partition with the ionising treatment radiation, wherein at least one trajectory is determined individually for each target region partition;

at least one electronic data storage device storing the medical image data and the predetermined concavity data, wherein the at least one processor is operably coupled to the at least one electronic data storage device for acquiring, from the at least one electronic data storage device, the medical image data and the predetermined concavity data; and the irradiation therapy device which is configured to emit a beam of ionising treatment radiation, wherein the at least one processor is operatively coupled to the irradiation therapy device so as to effect emission of the treatment radiation by the irradiation therapy device based on the irradiation trajectory data.

15. The system according to claim 14, wherein the at least one processor determines the image concavity data by determining the value of a concavity measure defined as a ratio of the volume of a convex hull of the target region and the volume of the target region.

16. The system according to claim 15, wherein the concavity is the topological concavity such that the convex hull is defined by all image units that lie on a straight line between any two image units of the at least part of the target region.

17. The system according to claim 14, wherein the at least one processor compares the value of the measure of the concavity described by the image concavity data to the value of the measure of the concavity described by the predetermined concavity data by determining whether the value of the measure of the concavity described by the image concavity data is greater than the predetermined value of the measure of the concavity described by the predetermined concavity data.

18. The system according to claim 17, wherein the at least one processor determines the partition boundary data in response to a determination that the value of the measure of the concavity described by the image concavity data is greater than the value of the measure of the concavity described by the predetermined concavity data.

* * * * *